United States Patent [19]
Klein et al.

[11] Patent Number: 5,908,162
[45] Date of Patent: Jun. 1, 1999

[54] SPRAY GUN HAVING AN ANTI-BACK-IONIZATION PROBE WITH A CONTROL SYSTEM THEREFOR

[75] Inventors: Richard G. Klein, Avon Lake; Gerald W. Crum, Elyria; Sergey V. Guskov, Rocky River, all of Ohio

[73] Assignee: Nordson Corporation, Westlake, Ohio

[21] Appl. No.: 09/030,590

[22] Filed: Feb. 25, 1998

[51] Int. Cl.⁶ .............................. B05B 5/00; G01N 27/60
[52] U.S. Cl. ..................... 239/691; 239/704; 239/708; 118/671; 324/452
[58] Field of Search ................. 239/690, 690.1, 239/691, 704, 706, 708; 324/455, 452; 118/629, 671

[56] References Cited

U.S. PATENT DOCUMENTS

| | | |
|---|---|---|
| 2,433,594 | 12/1947 | Calo . |
| 3,279,429 | 10/1966 | Félici et al. . |
| 3,558,052 | 1/1971 | Dunn . |
| 4,011,991 | 3/1977 | Masuda ................................. 239/708 |
| 4,568,027 | 2/1986 | Lazarus . |
| 4,713,257 | 12/1987 | Luttermöller . |
| 4,779,564 | 10/1988 | Kiefer et al. . |
| 4,921,172 | 5/1990 | Belmain et al. . |
| 5,063,350 | 11/1991 | Hemming et al. ...................... 324/457 |
| 5,351,903 | 10/1994 | Mazakas et al. ..................... 239/690 X |
| 5,584,931 | 12/1996 | Buhlmann . |
| 5,598,099 | 1/1997 | Castleman ............................. 324/456 |

FOREIGN PATENT DOCUMENTS

| | | |
|---|---|---|
| 0 574 305 | 12/1993 | European Pat. Off. . |
| 0 620 045 | 10/1994 | European Pat. Off. . |
| 856 361 | 3/1952 | Germany . |
| 35 10 199 | 10/1986 | Germany . |
| 40 22 643 | 11/1991 | Germany . |

OTHER PUBLICATIONS

Campbell, "Electrostatic charging of powder coating material," Finishing, Jun. 1994, pp. 28, 30.
Acker, "Corona coating of powder without the orange–peel effect," publication unknown, date, unknown.
Matsushita Electric, Patent Abstracts of Japan, vol. 017., No. 620 (E–1460), Nov. 16, 1993; relating to Japanese Patent Publication No. 05191689, published Jul. 30, 1993.

*Primary Examiner*—Andres Kashnikow
*Assistant Examiner*—Sean P. O'Hanlon
*Attorney, Agent, or Firm*—Rankin, Hill, Porter & Clark LLP

[57] ABSTRACT

A powder spray coating system includes a spray gun for spraying powder in a spray pattern onto a part. The spray gun includes an electrode connected to a power supply, the electrode charging powder as the powder is dispensed from the gun toward the part. A first current sensor measures gun current from the power supply to the electrode. An ABI probe or ion collector is mounted with the gun for collecting free ions produced by the electrode. The collector has a forward portion positioned near the spray pattern and spaced from the electrode. A second current sensor measures return current from the ion collector. A regulating assembly regulates the return current from the ion collecting device. A controller is connected to the first and second current sensors and to the regulating assembly for operating the regulating assembly in accordance with a predetermined setting representing the difference between the gun current and the return current. The system automatically adjusts the position or effective position of the forward tip of the ABI probe relative to tip of the gun as parts of different shapes and geometry pass before the gun.

24 Claims, 5 Drawing Sheets

SPRAY GUN HAVING AN ANTI-BACK-IONIZATION PROBE WITH A CONTROL SYSTEM THEREFOR

BACKGROUND OF THE INVENTION

1. Field of the Invention

This invention relates to electrostatic spray coating systems, and more particularly to a device for collecting free ions in an electrostatic spray coating system.

2. Description of the Prior Art

In electrostatic spray coating systems, the coating material is pumped from a supply to one or more spray guns which spray the coating material onto a part to be coated. The coating material may be either in the form of dry particles conveyed in a fluidized air stream or in the form of liquid atomized by the gun. The spray guns may charge the coating particles by means of a high voltage charging electrode. When the coating particles are sprayed from the front of the gun, they are electrostatically attracted to the part to be coated which is generally electrically grounded and suspended from an overhead conveyer or otherwise conveyed through a spray booth. The spray guns are mounted in the spray booth, either in a stationary position or on a reciprocator or other device which allows the gun to be automatically moved in a predetermined path. Once these charged coating particles are deposited onto the part, they adhere there by electrostatic attraction until they are conveyed into an oven where they are cured, or, in the case of powder coating, melted to flow together to form a continuous coating on the product.

An ion collector or counter-electrode has been found to be useful in attracting free ions which would otherwise flow from the gun to the ground part. When charging the powder, a large number of free ions are also generated. Without an ion collector, the free ions are conveyed with the coating material onto the part. This causes a charge to accumulate on the deposited coating layer until the local electric field strength is great enough to cause ionization within the coating layer. This "back-ionization" disturbs the deposited coating and results in craters and other defects in the cured coating. Back-ionization causes a dramatic reduction in transfer efficiency and has a detrimental effect on economic and environmental effectiveness of the powder coating process. By using an ion collector, these free ions are collected before they reach the part, the transfer efficiency is improved, and the appearance of the surface finish on the part can be improved.

An example of an ion collector is the anti-back-ionization (ABI) device shown in U.S. Pat. application Ser. No. 08/959,723 assigned to the assignee of the present invention. This patent shows an ABI probe which provides satisfactory free ion collection. The effective probe length is adjustable, allowing the position of the end of the probe relative to the electrode to be changed, so that the probe position relative to the electrode can be adjusted.

Another example of an ion collector is shown in U.S. Pat. No. 4,921,172, issued to Belmain et al., in the form of a counter-electrode mounted on a powder spray gun on the front of the gun. Yet another example of an ion collector is shown in European Patent Publication No. 0,620,045 in the form of a counter-electrode ring fixedly mounted around the front of the gun. These ion collectors are fixed in position or built into the gun, so that they do not provide easy adjustment or removability.

The presence of an ion collector or ABI device or probe allows users to dramatically reduce the field strength between the gun and the grounded part as well as significantly reduce the free ion current to the part. Therefore, the development of back ionization is reduced or delayed, and the strength of the electric field between the gun and part is reduced. The reduction in field strength results in improved penetration of recessed areas or Faraday cage areas on the part. Positioning the ABI probe, however, is very important in fully realizing the positive effects of the probe. If the ABI probe is positioned properly, the coating results are comparable to those achieved using statically charged coating systems, and the ease of application is similar.

Maintaining the proper distance between the tip of the ABI probe and the part, however is more difficult than might first be contemplated. The distance between the gun and the part changes based upon the geometry of the part and upon changes in the parts assortment. Many parts include recessed areas which are significantly farther from the gun than the remainder of the part, and many parts are presented on production lines mixed with other parts which have significantly different shapes. As the distance between the gun and part changes, the positioning of the ABI probe must be manually adjusted to provide for maximum positive effect of using the ABI probe as an ion collector. Unfortunately, manual re-positioning is usually not possible in the middle of a production run as different shaped parts enter the spray booth. While manual re-positioning can be performed periodically taking into account the general shape and geometry of the parts on a specific production run, such manual re-positioning of the ABI probe can be rather cumbersome and, as a result, tends to be done rarely in many production applications.

SUMMARY OF THE INVENTION

These and other problems are overcome by the control system for an anti-back-ionization device control system of the present invention. The invention provides a system for automatically adjusting the effective position of the forward surface of the ion collector or ABI probe relative to the charging electrode of the gun as parts of different shapes and geometry pass before the gun in a spray booth. This control system thus provides for maximum utilization of the benefits of an ABI probe or free ion collector in a powder spray coating system.

The ABI probe control system of the present invention allows users to automatically maintain the transfer current to the grounded part below a certain preset level and, therefore, keep the ion current from rising as the part comes nearer to the gun or as gun is moved closer to the part. Such control over the transfer current delays the development of back ionization on the part, as well as reducing the strength of the electric field between the gun and the part as the gun is moved closer to the part. The reduction in field strength, in turn, results in improved penetration of recessed areas on the part. The control system allows the attainment of maximal benefits of an ABI probe, improving the transfer efficiency, and improving the appearance of the surface finish on the part.

The ABI probe control system of the present invention also provides for automatic operation. Because the effective position of the ABI probe is automatically changed as the need for ion collection increases or decreases, there is no need for an operator to adjust any application parameters, nor is there a need for manual re-positioning of the ABI probe.

The control system of the present invention thus allows users to control automatically the current between the gun and the part by controlling field strength and current between the tip of the gun and the ABI probe, making it unnecessary to adjust the positioning of the ABI probe in order to maximize its benefits in situations where the distance between the gun and the part changes.

These and other advantages are provided by the present invention of a powder spray coating system, comprising: a power supply; a spray gun for spraying powder in a spray pattern onto a part, the spray gun including an electrode connected to the power supply, gun current being supplied from the power supply to the electrode, the electrode charging powder as the powder is dispensed from the gun toward the part; an ion collector mounted with the gun for collecting free ions produced by the electrode, the collector having a forward portion positioned near the spray pattern and spaced from the electrode, there being return current flowing from the ion collector toward ground; a regulating assembly which regulates the effective position of the ion collector relative to the electrode; and a controller connected to the regulating assembly for operating the regulating assembly in accordance with a predetermined setting representing the difference between the gun current and the return current.

DETAILED DESCRIPTION OF THE PREFERRED EMBODIMENT

Figure 1:
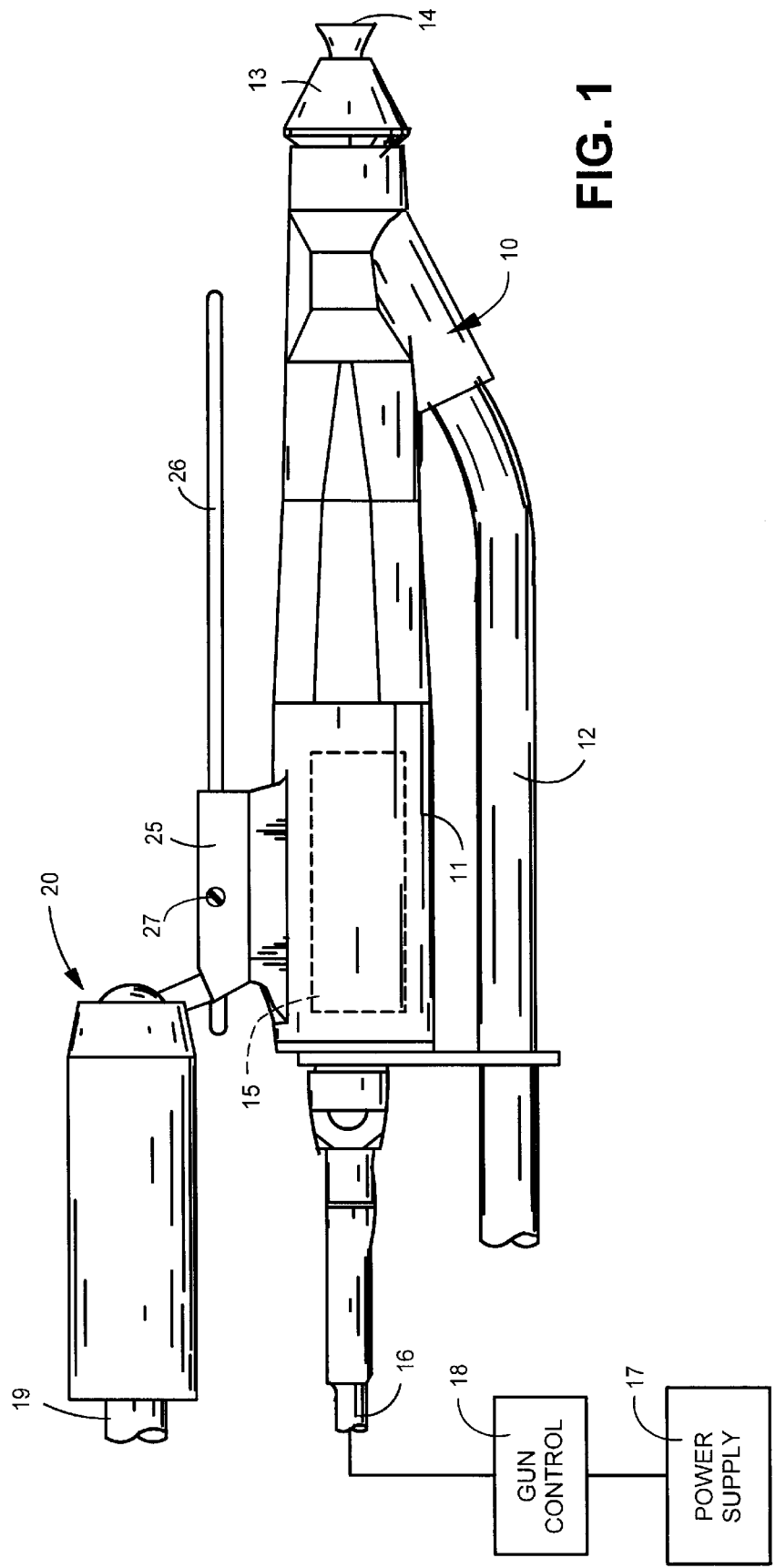
FIG. 1 is a side elevational view of a spray gun having an anti-back-ionization probe attached thereto.

Referring more particularly to the drawings and initially to FIG. 1, there is shown an automatic powder gun 10. The gun 10 is of the type commonly used to spray powder entrained in an air flow onto parts, and the gun includes a body 11, a supply hose 12 connected to the body 11 and supplying powder to the outlet nozzle 13 from which the powder is sprayed onto the parts. An electrical charge is imparted to the powder at the nozzle 13 by an electrode 14. The electrode 14 is typically charged to a large negative potential, for example −100 kV. The electrode 14 is connected to suitable high-voltage electrical supply components 15 located within the gun body 11 with low-voltage electricity supplied to the gun through an electrical supply line 16 which is connected to a low-voltage power supply 17. The voltage supplied to the electrode is controlled by a gun controller 18 which is connected between the supply line 16 and the low-voltage power supply 17. The gun 10 may be mounted on a mounting bar 19 by means of a gun mount assembly 20. Any suitable mounting assembly may be used, the preferred mounting assembly being that disclosed in U.S. Pat. application Ser. No. 08/959,723.

The gun mount assembly 20 includes a mounting plate 25 having a hole (not shown) extending through the mounting plate from the front face to the rear face of the mounting plate for mounting and supporting an ion collector or anti-back-ionization (ABI) probe 26. As shown in FIG. 1, the probe 26 may be a single rod of a strong, highly conductive material, such as brass or aluminum. The probe may be held in a fixed position by means a set screw 27 within the opening 25, or the probe may be made automatically movable as will be explained below with reference to FIGS. 3–6. The probe 26 may be directly grounded through the mounting plate 25, or the probe may be mounted within an insulated sheath (not shown) within the mounting plate so that it may be maintained at a regulated potential as will be further explained below with reference to FIGS. 2 and 7. At least the forward end of the probe 26 is rounded in a hemispherical shape.

While a rod-shaped probe 26 is shown in FIG. 1, the ABI probe or ion collector may be a surface with rounded edges spaced from the gun electrode. The desired shape and placement of the ion collector depend upon the electric field generated by the electrode and the desired ion collection function performed by the probe. The purpose of the ABI probe 26 is to collect free ions generated at the charging electrode 14 of the spray gun 10. The presence of the probe 26 in proximately to the electrode 14 also creates an electric field which is focused backwardly onto the probe in addition to the electric field which is created by the gun electrode 14 and which is focused forwardly onto the part. In order to collect most of the ions from the charging electrode of the gun, the distance between the tip of the probe and the tip of the charging electrode should have the proper relationship with the distance between the tip of the charging electrode and the part being sprayed. If this distance relationship is maintained, the electric field between the charging electrode 14 and the probe 26 will be stronger than the electric field between the charging electrode and the part.

By collecting ions with the probe 26 instead of allowing them to deposit on the part, the appearance of the surface finish on the part can be improved. Without the use of the ABI probe, charge would accumulate on the deposited powder layer as the part is sprayed until the local electric field strength is great enough to cause ionization within the powder layer. This "back-ionization" adversely affects transfer efficiency and the ability to coat uniformly Faraday cage areas. In addition, back-ionization could disturb the deposited powder and result in craters and other defects in the cured coating on the part. By using an ABI probe, these craters and defects are avoided, and a smoother coating is produced. Since the ABI probe collects the ions instead of allowing them to collect on the part, thicker coatings can be produced on the parts because incoming powder is not discharged as quickly by back-ionization of the charged powder deposited. The use of the ABI probe also makes it easier to apply a second coating to parts which have previously been coated because, as previously stated, there is a reduced charge build-up on the part.

Since the electric field which goes from the charging electrode of the gun to the part is weaker because of the ABI probe, the gun should apply a more uniform thickness coating onto the part without a thicker coating on the protruding parts and edges. Without the probe, the electric field lines would normally concentrate along edges closest to the gun, and a thick coating could result in these regions. The weaker field which results from the use of the ABI probe should also result in better coating of the Faraday cage areas on the parts without being diverted toward the closest edges by a strong electric field. A corona charging gun with an ABI probe should have similar spray characteristics to a tribocharging gun, since a tribocharging gun does not have a high voltage charging electrode, does not create as many ions, and does not create as strong an electric field between the gun and part.

Various other embodiments of the ABI probe can be used, and some of these are shown in the aforementioned U.S. Pat. application Ser. No. 08/959,723. While the probe 26 shown in FIG. 1 is a single rod of conductive material adjustably held by the set screw 27 in the mounting plate 25, the fixed length of the probe can also be varied by providing a set of different length probes, so the distance could be adjusted by removing a probe of one length and replacing it with another probe of a different length. Alternatively, the ABI probe may comprise one or more sections which may be assembled together as needed to create a probe of desired length. The ABI probe could be made in a telescoping design, similar to those used with retractable antennae. As a further alternative, instead of using the set screw 27 to hold the probe 26 in the opening 25, the probe could have an external thread along its length which matches the internal thread in the hole, so that the user could adjust the effective length of the probe simply by turning the probe clockwise or counterclockwise.

The ABI probe may be an elongated rod extending along the side of the gun body as shown in FIG. 1, but it may also be a conductive ring surrounding the gun at a desired distance from the tip of the gun electrode. The ABI probe or ion collector may also take the form of a smooth surface embodied into the outer shell of the gun body. Furthermore, while the ABI probe 26 shown in FIG. 1 is mounted to the mounting plate, the probe may alternatively be mounted directly onto the gun body at a location other than where the gun mount assembly 20 is attached to the gun. For manually operated spray guns, for example, the probe can be mounted on a bracket attached to the side or top of the gun.

In accordance with the present invention, the ABI probe or ion collector 26 is connected to a control system 32 which automatically adjusts the field strength between the tip of the charging electrode and the tip of the ABI probe by changing the effective position of the ABI probe as the distance between the gun and the part changes. The effective position of the ABI probe may be changed by changing the actual position of the probe or by changing the electric potential of the probe. One embodiment of this control system 32 is depicted in schematic form in FIG. 2. A first current sensing device 33 associated with the high voltage transformer 15 located within the gun measures the gun current $\mu A_1$ flowing from the low-voltage power supply 17 through the internal gun components 15 to the electrode 14. A second current sensing device 34 measures the return current $\mu A_3$ flowing back from the ABI probe to ground. The current sensors 33 and 34 may be any suitable current measurement device, such as a current probe, a measuring resistor, a Hall effect device or a micro-ammeter. The two current readings from the current sensors 33 and 34 are supplied on appropriate lead lines to an electronic logic unit 35 which determines the difference between the gun current and the return current readings, $\mu A_1 - \mu A_3$. This difference $\mu A_1 - \mu A_3$ is equal to the transfer current $\mu A_2$, which is the current "delivered" by the powder particles to the part 36, plus the current lost during the spray coating operation. In other words, in order to maintain the transfer current $\mu A_2$ constant, the difference $\mu A_1 - \mu A_3$ should be equal to a constant.

Figure 2:
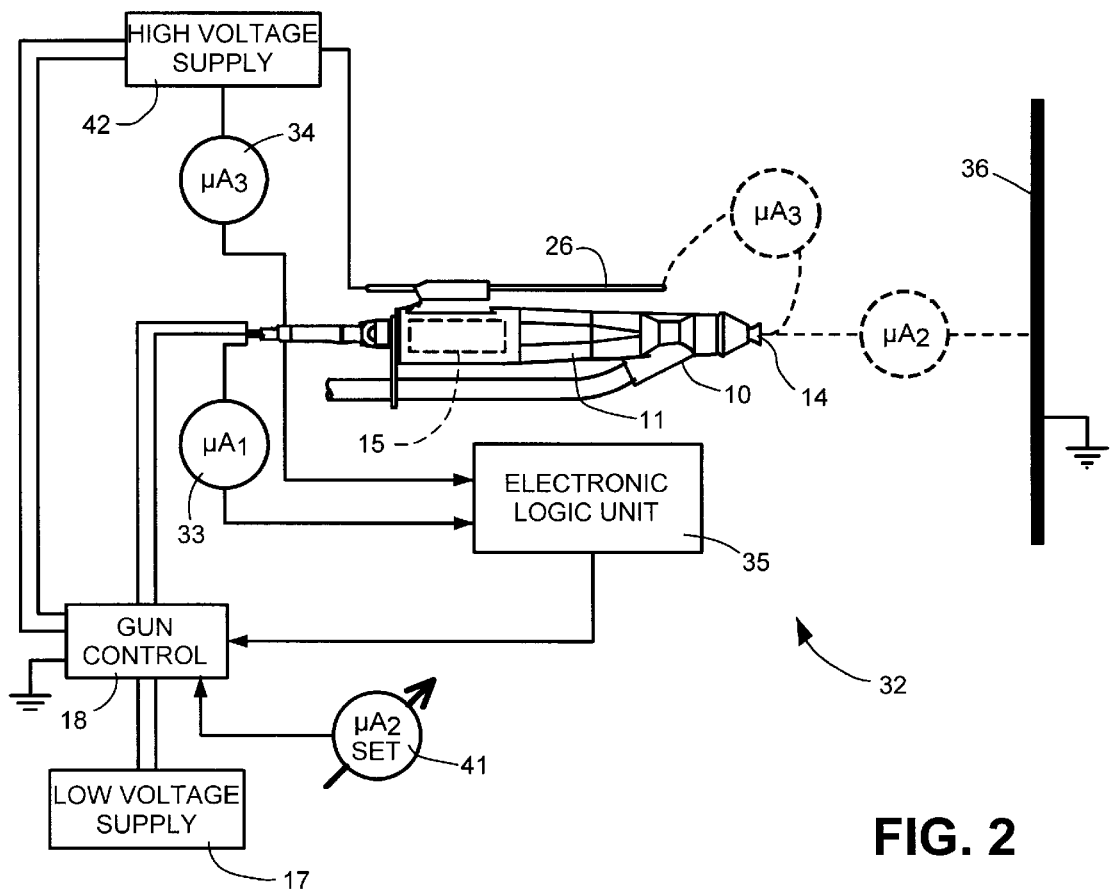
FIG. 2 is a schematic view of one embodiment of a control system in accordance with the present invention.

In accordance with this invention, the return current $\mu A_3$ is controlled by the gun controller 18 so that the difference $\mu A_1 - \mu A_3$ is maintained at a constant level. The constant level of this difference $\mu A_1 - \mu A_3$ may be input to the gun controller by means of a transfer current $\mu A_2$ input 41. The return current $\mu A_3$ is then maintained by the gun controller at a level such as to keep the difference $\mu A_1 - \mu A_3$ at a constant set level. The return current $\mu A_3$ may be controlled in any one of several different ways. In FIG. 2, the return current $\mu A_3$ is controlled by means of a high-voltage power supply 42 located between the ABI probe 26 and ground. The power supply 42 is connected to the gun controller 18 which supplies a low voltage input to the supply. The power supply 42 takes the low voltage input and acts as a multiplier to transform the input supply to a high voltage output which is supplied to the ABI probe 26. The power supply 42 adjusts the potential of the ABI probe 26 to a desired voltage level in order to increase or decrease the field strength between the gun electrode and the ABI probe, and thus control the level of the current $\mu A_3$ passing through the ABI probe to ground. The second current sensor 34 is thus associated with the power supply 42 and measures the current flowing back from the ABI probe 26 to an eventual ground through the supply 42.

In operation, the user sets a desired transfer current $\mu A_2$ into the gun controller 18 at the input 41. As a part passes before the gun, the current sensor 33 measures the gun current $\mu A_1$ flowing to the electrode, and the second current sensor 34 measures the return current $\mu A_3$ flowing from the ABI probe 26. The difference between the currents, $\mu A_1 - \mu A_3$, is compared in the electronic logic unit 35 to a constant value calibrated to be proportional to the set transfer current $\mu A_2$. If this current difference $\mu A_1 - \mu A_3$ is not approximately the same as the constant value, the gun controller 18 adjusts the multiplier 42 to increase or decrease the voltage of the ABI probe 26. Increasing or decreasing the positive potential at the forward tip of the ABI probe 26 is equal in its effect to changing the distance between the forward tip of the probe and the electrode 14. Here, the greater the difference of potentiality between the electrode and the ABI probe, the stronger the field between the tip of the electrode and the tip of the ABI probe and the weaker the strength of the field created by the gun between the gun and the part. This process is constantly repeated as differently shaped parts enter the spray booth to be coated or even during the coating of a single part if the part includes a large recessed area which would otherwise have a significant effect on the distance between the gun and the portion of the part being coated.

Figure 3:
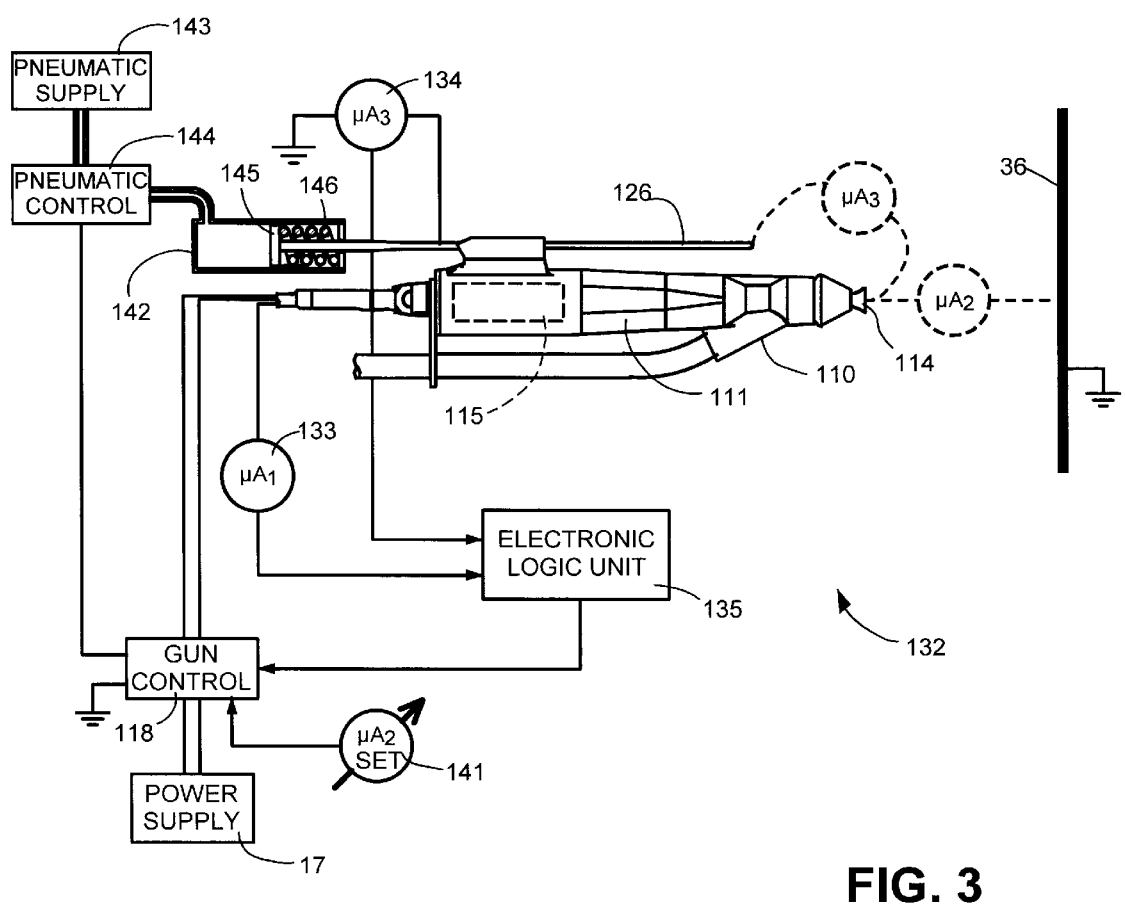
FIG. 3 is a schematic view similar to FIG. 2 of another embodiment of the control system of the present invention.

Other means may be employed to control the level of the return current $\mu A_3$. FIG. 3 shows a control system 132 in which the position of the forward tip of the ABI probe may be automatically adjusted rather than adjusting the potential of the probe. The control system 132 of FIG. 3 has a gun 110 having a gun body 111 and internal high-voltage components 115, a gun controller 118, an ABI probe 126, a first current sensor 133, a second current sensor 134, an electronic logic unit 135, and an input 141 which are essentially identical to the gun 10, the gun body 11, the high-voltage components 15, the gun controller 18, the ABI probe 26, the first current sensor 33, the second current sensor 34, the electronic logic unit 35 and the input 41 of FIG. 2. Instead of a high voltage supply or multiplier 42, the embodiment shown in FIG. 3 uses a pneumatic cylinder 142 for moving the longitudinal position of the ABI probe 126 relative to the body of the gun 110. The cylinder 142 is connected to a pneumatic supply 143 by means of a pneumatic control 144, so that the piston 145 in the cylinder 142 may be actuated one direction to advance the longitudinal position of the ABI probe, or actuated in the other direction to retract the ABI probe by means of a return spring 146 which retracts the piston when the pneumatic pressure in the cylinder is reduced. Unlike the probe 26 in the control system 32 of FIG. 2, the ABI probe 126 is always grounded. The ABI probe 126 is also connected to the current sensor 134 which measures the current $\mu A_3$ flowing back from the ABI probe to ground. The current sensor 133 associated with the internal gun transformer 115 measures the current $\mu A_1$ flowing from the power supply 117 to the electrode 114. The electronic logic unit 135 determines the difference between these two current readings, $\mu A_1 - \mu A_3$. As with the control system 32, the return current $\mu A_3$ is controlled by the gun controller 118 so that the difference $\mu A_1 - \mu A_3$ is maintained at a preset level in accordance with the $\mu A_2$ current input 141. The gun controller maintains the return current $\mu A_3$ so as to keep the difference $\mu A_1 - \mu A_3$ at a constant set level by using the pneumatic control 144 to regulate the pneumatic pressure to the cylinder 142. The ABI probe 126 is moved forward toward the electrode 114 to increase the return current $\mu A_3$, and the ABI probe is retracted to decrease the return current $\mu A_3$.

In operation of the control system 132 of FIG. 3, the user sets a desired transfer current $\mu A_2$ into the gun controller 118 at the input 141. As a part passes before the gun, the first current sensor 133 measures the current $\mu A_1$, the second current sensor 134 measures the current $\mu A_3$, and the electronic logic unit 135 measures the difference between the currents, $\mu A_1 - \mu A_3$, and compares the difference to a constant value calibrated to be proportional to the set current $\mu A_2$. If this current difference is not approximately the same as the constant value, the gun controller 118 actuates the pneumatic control 144 to increase or decrease the pressure to the cylinder 142 to move the ABI probe 126 closer to the electrode or farther away from the electrode, thereby to adjust the return current $\mu A_3$ and, therefore, regulate the transfer current $\mu A_2$. This process is constantly repeated as different shaped parts 36 enter the spray booth to be coated or even during the coating of a single part if the part includes a large recessed area which would otherwise have a significant effect on the distance between the gun and the portion of the part being coated.

Figure 4:
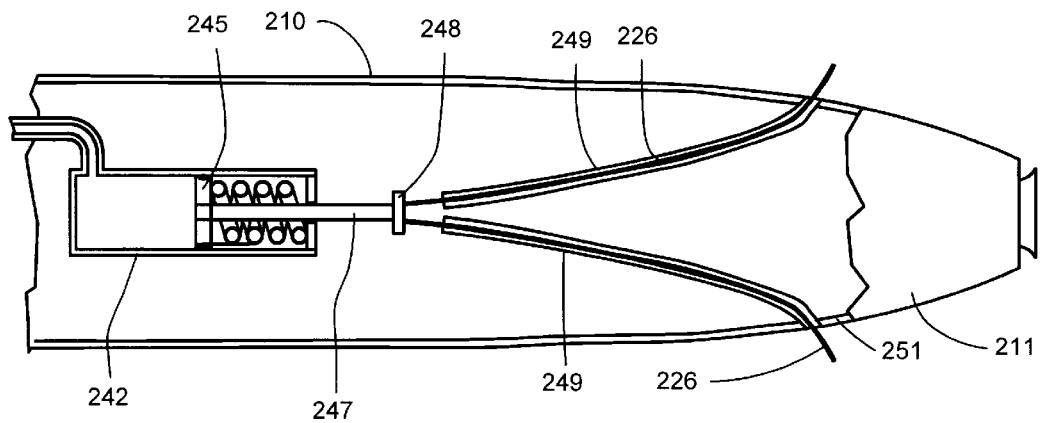
FIG. 4 is a schematic view of a variation of anti-back-ionization probe for use in the control system of FIG. 3.
Figure 5:
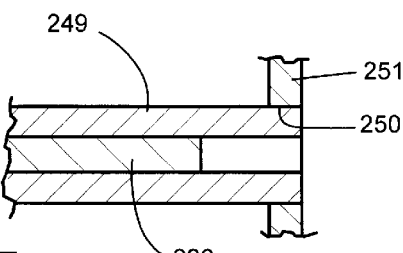
FIG. 5 is a detailed view of a portion of FIG. 4 showing the exit of the ABI probe from the gun body.
Figure 6:
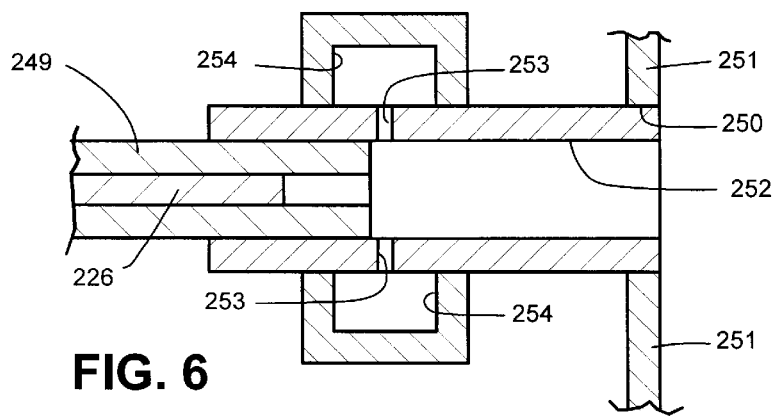
FIG. 6 is detailed view similar to FIG. 6 showing an alternative arrangement for the exit of the ABI probe from the gun body.

An alternative embodiment for providing an ABI probe which can be moved relative to the electrode is shown in FIGS. 4–6. This embodiment uses a pneumatic cylinder 242 located with the body 211 of the gun 210 as shown in FIG. 4. The cylinder 242 has a piston 245 which is connected to a piston rod 247. A yoke assembly 248 is mounted to the forward end of the piston rod 247. A pair of wires 226 which comprise the ABI probe are connected to the yoke assembly 248, and each of the wires 226 extend through a plastic sheath 249 to the exterior of the gun along the sides of the gun body 211 spaced from the gun electrode 214. The wire 226 may extend through an opening 250 in the gun body wall 251 with a zero clearance as shown in FIG. 5, which shows the wire 226 fully retracted. Alternatively, the wire 226 may extend through an air shroud as shown in FIG. 6 in which a bore 252 is provided in the gun body wall 251, with air holes 253 around the bore 252. The air holes 253 may be connected through an air galley 254 to a pressurized air supply (not shown) so that pressurized air flows through the galley 254 and through the air holes 253 in the bore and shrouds the wire 226 with air to allow the wire to move freely through the bore 252 and to help prevent accumulations of powder from clogging the bore and inhibiting movement of the wire.

Figure 7:
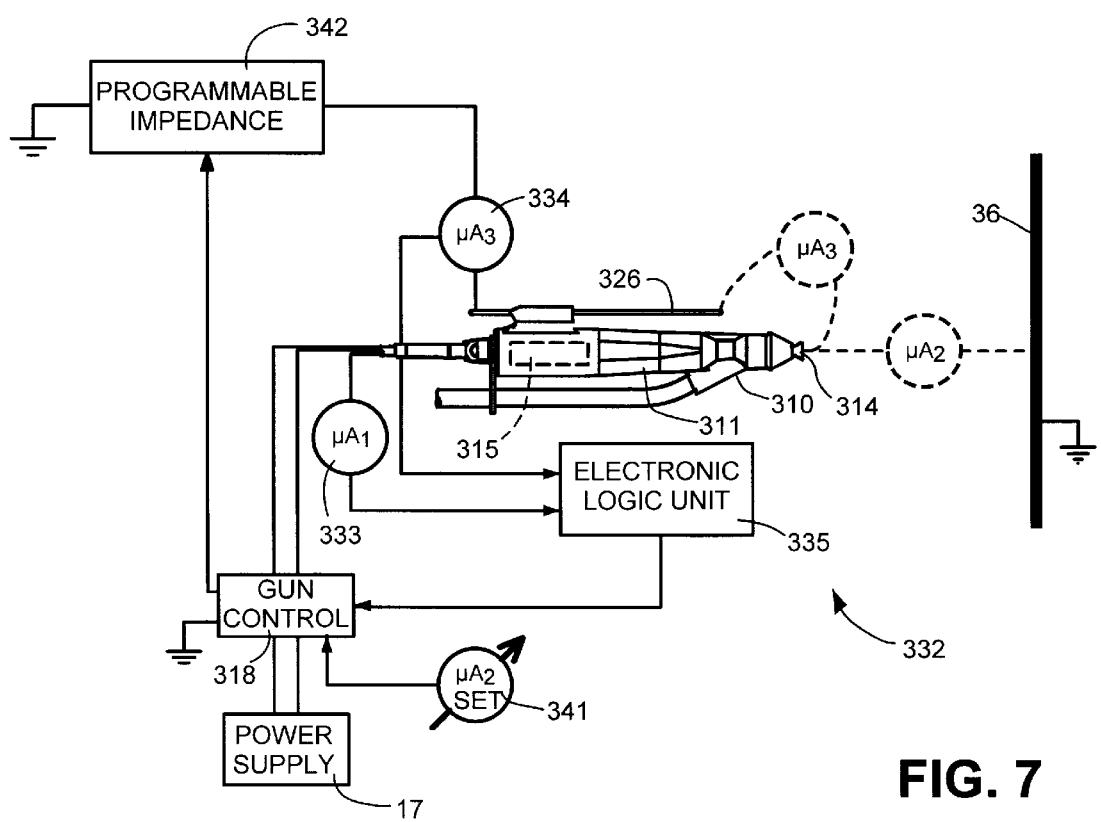
FIG. 7 is a schematic view similar to FIGS. 2 and 3 of yet another embodiment of the control system of the present invention.

Another embodiment of the control system is shown in FIG. 7. The control system 332 of FIG. 7 has a gun 310 having a gun body 311 and internal high-voltage components 315, a gun controller 318, an ABI probe 326, a first current sensor 333, a second current sensor 334, an electronic logic unit 335, and an input 341 which are essentially identical to the gun 10, the gun body 11, the high-voltage components 15, the gun controller 18, the ABI probe 26, the first current sensor 33, the second current sensor 34, the electronic logic unit 35 and the input 41 of FIG. 2. In the control system 332, the ABI probe 326 is connected to ground through a variable resistance device 342. The variable resistance device 342 may be any suitable device which is capable of being used in the high voltage environment of a electronic static powder spray system which may encounter voltages on the level of ±100 kV. Such a resistance device would typically include an oil bath to insulate the resistance device and provide adequate cooling. The variable resistance device 342 is connected to the gun controller 318 so that the gun controller can regulate the return current $\mu A_3$ measured by the current sensor 334 by changing the resistance. The current sensor 333 associated with the internal high-voltage gun components 315 measures the electrode current $\mu A_1$. The electronic logic unit 335 determines the current difference $\mu A_1 - \mu A_3$ and compares this difference with the $\mu A_2$ current input 341. The return current $\mu A_3$ is then maintained by the gun controller by changing the resistance between the ABI probe 326 and ground by means of the variable resistance device 342. As each part 36 passes before the gun 310, if the current difference is not approximately the same as the constant value, the gun controller 318 adjusts the variable resistance device 342 which effectively increases or decreases the voltage of the ABI probe 326. Changing this resistance is equal in its effect to changing the distance between the tip of the ABI probe and the gun electrode. Here, the higher the resistance between the ABI probe 326 and ground, the greater the positive potential at the tip of the ABI probe, the stronger the field between the tip of the gun and the tip of the ABI probe and the weaker the strength of the field created by the gun between the gun and the part. This process is constantly repeated as different shaped parts 36 enter the spray booth to be coated or even during the coating of a single part if the part includes a large recessed area which would otherwise have a significant effect on the distance between the gun and the portion of the part being coated.

All of the previously described embodiments of the control system of the present invention have common advantages. The control system provides an automatic feedback circuit that allows users to maintain automatically the supply current to the gun electrode as such levels as to keep the current from the electrode to the part being coated from rising as the gun is moved closer to the part. This control over the gun current delays the development of back ionization on the part, and prevents an increase in the strength of the electric field between the gun and the part as the gun is moved closer to the part. The reduction in field strength, in turn, results in improved penetration of spray powder into recessed areas on the part. The automatic feedback circuit operates automatically, and there is no need for an operator to adjust any application parameters.

A benefit of the ABI probe is that it allows users to dramatically reduce the field strength between the gun and the grounded part as well as practically eliminate the free ion current to the part. Therefore, development of back ionization is greatly delayed and penetration of Faraday cage areas is greatly facilitated. In fact, if the ABI probe is positioned properly, the distance between the tip of the gun and the ABI probe is approximately half of the distance between the gun and the part, the same ease of coating of recessed areas can be observed with corona guns as is achieved in tribo applications.

One shortcoming of the ABI probe is that the distance between the gun and the part changes based on the geometry of the part and on changes in the parts assortment. As this distance changes, the positioning of the ABI probe behind the top of the gun must be manually adjusted to provide for maximum positive effect of using the ABI probe as an ion collector. Unfortunately, such manual repositioning of the ABI probe can be rather cumbersome and, as a result, tends to be rarely done in production applications.

The technology that would allow users to automatically control the current between the gun and the part by controlling field strength and current between the tip of the gun and the ABI probe would also make it unnecessary to adjust the positioning of the ABI probe in order to maximize its benefits in situations where the distance between the gun and the part changes.

While the control systems shown in FIGS. 2, 3 and 7 are essentially closed-loop systems in which the target current is determined using measurements of the supply current and the return current, it is also possible to use the principles of the present invention in an open loop system in which an approximate return current can be determined through experimentation or through experience, and the effective position of the ABI probe (meaning either the actual position of the probe or the voltage supplied to a static probe), can be varied depending upon the actual part being coated. While such an open loop system would not produce results as satisfactory as the closed loop system described herein, it may be easier to implement in existing spray coating systems.

Other variations and modifications of the specific embodiments herein shown and described will be apparent to those skilled in the art, all within the intended spirit and scope of the invention. While the invention has been shown and described with respect to particular embodiments thereof, these are for the purpose of illustration rather than limitation. Accordingly, the patent is not to be limited in scope and effect to the specific embodiments herein shown and described nor in any other way that is inconsistent with the extent to which the progress in the art has been advanced by the invention.

What is claimed is:

1. A powder spray coating system, comprising:
   a power supply;
   a spray gun for spraying powder in a spray pattern onto a part, the spray gun including an electrode connected to the power supply, gun current being supplied from the power supply to the electrode, the electrode charging powder as the powder is dispensed from the gun toward the part;
   an ion collector mounted with the gun for collecting free ions produced by the electrode, the collector having a portion positioned in spaced relationship from the electrode, there being return current flowing from the ion collector toward ground;
   a regulating assembly which regulates the effective position of the ion collector relative to the electrode; and
   a controller connected to the regulating assembly for operating the regulating assembly.

2. A powder spray coating system as defined in claim 1, wherein the controller operates the regulating assembly in accordance with a predetermined setting representing the difference between the gun current and the return current.

3. A powder spray coating system as defined in claim 2, wherein the effective position of the ion collector is regulated by changing the potential of the ion collector.

4. A powder spray coating system as defined in claim 3, wherein the regulating assembly comprises a variable voltage source connected to the ion collector to maintain the ion collector at a desired potential, the variable voltage source being connected to the controller to adjust the voltage level of the collector in accordance with the predetermined setting representing the difference between the gun current and the return current.

5. A powder spray coating system as defined in claim 3, wherein the regulating assembly comprises a variable resistance device connected between the collector and ground, the variable resistance device being connected to the controller to adjust the resistance in accordance with the predetermined setting representing the difference between the gun current and the return current.

6. A powder spray coating system as defined in claim 2, wherein the effective position of the ion collector is regulated by changing the actual position of the ion collector.

7. A powder spray coating system as defined in claim 6, wherein the regulating assembly comprises a driving device which moves the position of at least said portion of the collector relative to the electrode, and wherein the collector is grounded, the driving device connected to the controller to adjust the position of said portion of the collector in accordance with the predetermined setting representing the difference between the gun current and the return current.

8. A powder spray coating system as defined in claim 2, comprising in addition a first current sensor which measures the gun current from the power supply to the electrode and a second current sensor which measures return current from the ion collector, the controller connected to the first and second current sensors for changing the regulating assembly in accordance with the difference between actual current readings and the predetermined setting.

9. A powder spray coating system, comprising:
   a power supply;
   a spray gun for spraying powder in a spray pattern onto a part, the spray gun including an electrode connected to the power supply, the electrode charging powder as the powder is dispensed from the gun toward the part;
   a first current sensor which measures gun current from the power supply to the electrode;
   an ion collector mounted with the gun for collecting free ions produced by the electrode, the collector having a forward portion positioned in a spaced relationship from the electrode;
   a second current sensor which measures return current from the ion collector;
   a regulating assembly which regulates the return current from the ion collecting device; and
   a controller connected to the first and second current sensors and to the regulating assembly for operating the regulating assembly.

10. A powder spray coating system as defined in claim 9, wherein the controller operates the regulating assembly in accordance with a comparison of a predetermined transfer current setting and the actual difference between the gun current and the return current readings from the current sensors.

11. A powder spray coating system as defined in claim 10, wherein the regulating assembly comprises a variable voltage source connected to the ion collector to maintain the ion collector at a desired potential, the variable voltage source being connected to the controller to adjust the voltage level of the collector in accordance with the comparison of the predetermined transfer current setting and the actual difference between the gun current and the return current readings from the current sensors.

12. A powder spray coating system as defined in claim 20, wherein the regulating assembly comprises a driving device which moves the position of at least the forward portion of the collector relative to the electrode, and wherein the collector is grounded, the driving device connected to the controller to adjust the position of the forward portion of the collector in accordance with the comparison of the predetermined transfer current setting and the actual difference between the gun current and the return current readings from the current sensors.

13. A powder spray coating system as defined in claim 10, wherein the regulating assembly comprises a variable resistance device connected between the collector and ground, the variable resistance device being connected to the controller to adjust the resistance in accordance with the comparison of the predetermined transfer current setting and the actual difference between the gun current and the return current readings from the current sensors.

14. A powder spray coating system as defined in claim 9, comprising in addition an input device for inputting a setting corresponding to a desired transfer current to which the difference between the gun current and the return current is compared by the controller.

15. An electrostatic spray gun assembly as defined in claim 9, wherein the ion collector is an elongated rod.

16. An electrostatic spray gun assembly as defined in claim 9, wherein the gun comprises an elongated body having a longitudinal axis, and the collector extends generally parallel to the longitudinal axis of the gun body.

17. An electrostatic spray gun assembly as defined in claim 9, wherein the collector is spaced from the gun body.

18. A powder spray coating system, comprising:
   a power supply;
   a spray gun for spraying powder in a spray pattern onto a part, the spray gun including an electrode connected to the power supply, the electrode charging powder as the powder is dispensed from the gun toward the part;
   a first current sensor which measures gun current from the power supply to the electrode;
   an ion collector fixedly mounted with the gun for collecting free ions produced by the electrode, the collector having a forward portion positioned in a spaced relationship from the electrode;
   a second current sensor which measures return current from the ion collector;
   a regulating assembly connected between the ion collector and ground which regulates the return current from the ion collecting device to ground; and
   a controller connected to the first and second current sensors and to the regulating assembly for operating the regulating assembly.

19. A powder spray coating system as defined in claim 18, wherein the controller operates the regulating assembly in accordance with a comparison of a predetermined setting representing a desired transfer current and the difference between the measured gun current and the measured return current from the current sensors.

20. A powder spray coating system as defined in claim 19, wherein the regulating assembly comprises a variable voltage source connected to the ion collector to maintain the ion collector at a desired potential, the variable voltage source being connected to the controller to adjust the voltage level of the collector in accordance with the comparison of the predetermined setting and the difference between the measured gun current and the measured return current.

21. A powder spray coating system as defined in claim 19, wherein the regulating assembly comprises a variable resistance device connected between the collector and ground, the variable resistance device being connected to the controller to adjust the resistance in accordance with the comparison of the predetermined setting and the difference between the measured gun current and the measured return current.

22. A powder spray coating system as defined in claim 19, comprising in addition an input device for inputting setting corresponding to a desired transfer current to the difference between the measured gun current and the measured return current is compared.

23. A powder spray coating system, comprising:
   a power supply;
   a spray gun for spraying powder in a spray pattern onto a part, the spray gun including an electrode connected to the power supply, the electrode charging powder as the powder is dispensed from the gun toward the part;
   a first current sensor which measures gun current from the power supply to the electrode;
   an ion collector movably mounted relative to the gun for collecting free ions produced by the electrode, the ion collector being grounded, the collector having a forward portion positioned near the spray pattern and spaced from the electrode;
   a second current sensor which measures return current from the ion collector;
   a regulating assembly which moves the ion collector relative to the electrode to regulate the return current from the ion collecting device to ground; and
   a controller connected to the first and second current sensors and to the regulating assembly for operating the regulating assembly in accordance with a comparison of a predetermined setting representing a desired transfer current and the difference between the measured gun current and the measured return current from the current sensors.

24. A powder spray coating system as defined in claim 23, comprising in addition an input device for inputting a setting corresponding to a desired transfer current to which the difference between the gun current and the return current is compared by the controller.

* * * * *

UNITED STATES PATENT AND TRADEMARK OFFICE
CERTIFICATE OF CORRECTION

PATENT NO : 5,908,162
DATED : June 1, 1999
INVENTOR(S) : Klein et al.

It is certified that error appears in the above-identified patent and that said Letters Patent is hereby corrected as shown below:

Column 11, line 3, "20" should be --10--.
Column 11, line 21, "9" should be --10--.

Signed and Sealed this

Twenty-second Day of August, 2000

Attest:

Q. TODD DICKINSON

*Attesting Officer*  *Director of Patents and Trademarks*